United States Patent
Santa et al.

(10) Patent No.: US 6,583,298 B1
(45) Date of Patent: Jun. 24, 2003

(54) PROCESS FOR THE SYNTHESIS OF 17β-HYDROXY-17α-METHYL-2-OXA-5α-ANDROSTANE-3-ONE

(75) Inventors: Csaba Santa, Budapest (HU); Zoltan Tuba, Budapest (HU); Sandor Maho, Budapest (HU); Janos Szeles, Budapest (HU); Katalin Ferenczi, Budapest (HU); Peter Horvath, Budapest (HU); Krisztina Lancos, Budapest (HU); Tamas Mester, Budapest (HU); Arpad Trompler, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 0 days.

(21) Appl. No.: 10/030,742

(22) PCT Filed: May 26, 2000

(86) PCT No.: PCT/HU00/00048

§ 371 (c)(1),
(2), (4) Date: Nov. 30, 2001

(87) PCT Pub. No.: WO00/77025

PCT Pub. Date: Dec. 21, 2000

(30) Foreign Application Priority Data

Jun. 10, 1999 (HU) ............................................. 9901938

(51) Int. Cl.[7] ...................... C07D 313/04; C07D 311/00
(52) U.S. Cl. ...................................... 549/232; 549/276
(58) Field of Search ................... 549/276, 232

(56) References Cited

U.S. PATENT DOCUMENTS

| | | |
|---|---|---|
| 3,101,349 A | 8/1963 | Pappo |
| 3,109,016 A | 10/1963 | Nysted |
| 3,128,283 A | 4/1964 | Pappo et al. ................ 549/276 |
| 3,155,684 A | 11/1964 | Pappo |
| 3,282,962 A | 11/1966 | Pappo |

OTHER PUBLICATIONS

FR M 1697 (as the abstract of Chem. Abstracts, 59, 14067e.
JP 70 05, 773 (as the abstract of Chem. Abstracts, 72, 111706r.
Tetrahedron Letters No. 9, pp. 365–371 (1962).
Synthese Von Anhidriden Der A–Seco–Steroidreihe . . . by Snatzke et al. Liebigs Ann.Chem(1979) p. 1028–1039.
Photoinduced Molecular Transformations . . . by Suginome et al., J. Chem Soc. Perkin Trans(1990) p. 1239–1245.
Regioselektive Reduktionen . . . by Stanetty et al., Monatshefte fur Chemie 117, (1986) p. 69–88.
Heterocyclic Steroids, . . . by Zanatai et al. , Journal of Medicinal Chemistry, 1971, vol. 14, No. 10, p. 958–971.

Primary Examiner—Alan L. Rotman
Assistant Examiner—Raymond Covington
(74) Attorney, Agent, or Firm—Herbert Dubno Jonathan Myers

(57) ABSTRACT

The invention relates to a new process for the synthesis of 17β-hydroxy-17α-methyl-2-oxa-5α-androstane-3-one of formula (I). The process according to the invention is as follows: the 17β-hydroxy-17α-ethyl-1,3-seco-2-nor-5α-androstane-1,3-diacid of formula (III) is transformed into the ring-closed 17β-hydroxy-17α-methyl-1,3-seco-2-nor-5α-androstane-1,3-diacid anhydride of formula (II) in an inert solvent or without solvent with a $C_2$–$C_3$ alkan acid anhydride or a substituted carbodiimide of formula $R^1$—N=C=N—$R^2$— wherein $R^1$ and $R^2$ independently are $C_1$–$C_6$ alkyl group, $C_1$–$C_6$ alkyl group substituted by tertiary or quaternary amino group or 1–3 phenyl group, $C_5$–$C_6$ cycloalkyl group, aryl group substituted by 1–3 methoxy, tertiary amino, nitro, $C_1$–$C_4$ alkyl group or 1–3 halogen atom—and the obtained compound of formula (II) is reduced regioselectively by a complex alkali metal hydride in an inert solvent The new 17β-hydroxy-17α-methyl-1,3-seco-2-nor-5α-androstane-1,3-diacid anhydride of formula (II) is also the subject of the invention.

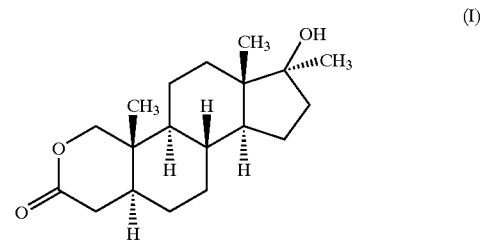

(I)

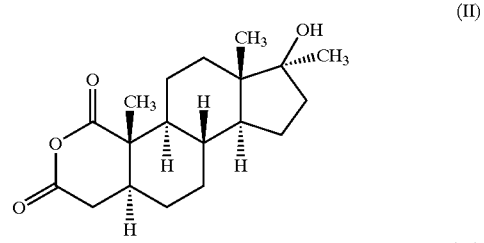

(II)

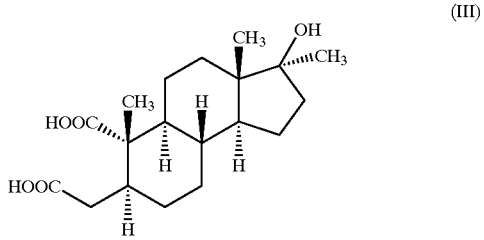

(III)

12 Claims, No Drawings

PROCESS FOR THE SYNTHESIS OF 17β-HYDROXY-17α-METHYL-2-OXA-5α-ANDROSTANE-3-ONE

The invention relates to a new process for the synthesis of 17β-hydroxy-17α-methyl-2-oxa-5α-androstane-3-one of the formula (I)

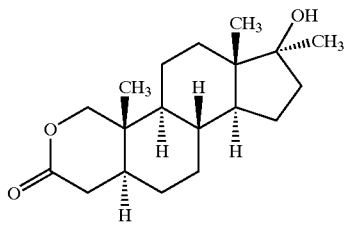

(I)

called further as oxandrolone—from 17β-hydroxy-17α-methyl-1,3-seco-2-nor-5α-androstane-1,3-diacide of formula (III)

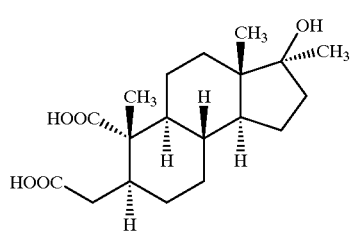

(III)

called further as secodicarboxylic acid.

The invention relates furthermore to the new 17β-hydroxy-17α-methyl-1,3-seco-2-nor-5α-androstane-1,3-diacid anhydride, too.

The oxandrolone is an anabolic, which is used in pediatrics and for mitigation of loss of weight developed as a consequence of infections, traumas and surgical intervention and recently for improvement of the condition of AIDS patients.

The synthesis of oxandrolone is described in several patents, i.e. the U.S. Pat. Nos. 3,101,349, 3,128,283 and 3,155,684, the German patent No. 1,171,425 and the French patent No. M1697. These patents describe the oxidation of 17β-hydroxy-17α-methyl-5α-androst-1-ene-3-one by lead tetraacetate in the presence of osmium tetroxide, when 17β-hydroxy-17α-methyl-1-oxo-1,3-seco-2-nor-5α-androstane-3-acid is obtained. In the next step of the reaction sequence the aldehyde group is reduced by sodium borohydride to furnish the hydroxymethyl group and the desired compound is synthesised from the obtained A-nor-hydroxy carboxylic acid by ring closure reaction. The descriptions do not give yields. The use of lead tetraacetate and especially the osmium tetroxide is extremely dangerous for health and not environmental friendly. We note, that the synthesis of the starting material, the 17β-hydroxy-17α-methyl-5α-androst-1-ene-3-one, can be carried out only in low yield by bromnination of 17β-hydroxy-17α-methyl-5α-androstane-3-one and subsequent hydrogen bromide elimination. This procedure is described i.e. in the U.S. Pat. No. 3,128,283.

According to the U.S. Pat. No. 3,109,016 the oxidation of the above mentioned starting material is carried out by ozone in carbon tetrachloride to yield the mixed anhydride of 17β-hydroxy-17α-methyl-1-oxo-1,3-seco-2-nor-5α-androstane-3-acid formed with formic acid, which is closed to a ring after reduction of the aldehyde group with sodium borohydride as described above. The oxidation was also carried out in dichloromethane in the presence of methanol to yield the methyl ester of the seco compound. The patent description does not give yields. As the use of carbon tetrachioride is restricted because of its harmful effect to health, the synthesis can not be used on industrial scale.

In the procedure described in the U.S. Pat. No. 3.282,962 the seco compound and the ring-closed oxandrolone are obtained as by-products and the latter is separated by crystallisation.

According to the Japanese patent No. 7,005,773 the desired compound is obtained by oxidation with perbenzoic acid from 17α-methyl-A-nor-5α-androstane-17β-ol-2-one. The above starting material can be synthesised from the 2,3-seco-diacid anhydride: by pyrolysis. The procedure is not economical and difficult to carry out even for the synthesis of lab scale quantities.

The paper, Tetrahedron Letters 9, 365–371 (1962), describes the oxidation by lead tetraacetate/osmium tetroxide and the subsequent reduction.

In the J. Med. Chem 14(10), 958–61 (1971) the cyclization coupled with acetylation of 17-hydroxy-seco-steroid diacids is shown.

J. Chem. Soc. Perkin Trans 1 no. 5., 1239–1245 (1990) shows the reduction of oxo group of D-homo-aza-steroids.

It can be seen from the above mentioned facts, that although there is need for oxandrolone in therapeutic use, its synthesis is not an industrially applicable, environmental friendly, harmless procedure.

Surprisingly it was found that our following process does not have the disadvantages of the known procedures, can be used industrially, is easily realisable, environmental friendly and the very pure final product, which fulfil the high standard of the present requirement of purity, can be obtained in good yield.

According to our process the secodicarboxylic acid of formula (III) is transformed into the ring-closed dicarboxylic anhydride (secodicarboxylic anhydride) of formula (II)

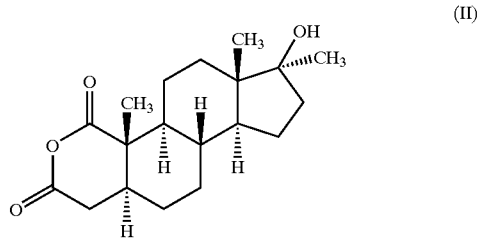

(II)

in an inert solvent with a $C_2$–$C_3$ alkane acid anhydride or a substituted carbodiimide of formula $R^1$—N=C=N—$R^2$— wherein $R^1$ and $R^2$ independently are $C_1$–$C_6$ alkyl group, $C_1$–$C_6$ allyl group substituted by tertiary or quaternary amino group or 1–3 phenyl group, $C_5$–$C_6$ cycloalkyl group, aryl group substituted by 1–3 nmethoxy, tertiary amino, nitro, $C_1$–$C_4$ alkyl group or 1–3 halogen atom and the obtained secodicarboxylic anhydride of formula (II) is reduced regioselectively by a complex alkali metal hydride in an inert solvent.

When the secodicarboxylic anhydride is obtained in the reaction with $C_2$–$C_3$ alkane acid anhydride in an inert solvent, the reduction can be carried out without isolation of the obtained secodicarboxylic anhydride by reacting it with a solution of a complex alkali metal hydride dissolved in an inert solvent The first step of the process according to our invention is preferably carried out by dissolving the secodicarboxylic acid in tetrahydrofuran and after addition of acetic anhydride, refluxing the reaction mixture until the completion of the reaction, evaporating the tetrahydrofuran and crystallisation of the obtained secodicarboxylic anhydride from diisopropyl ether. Instead of acetic anhydride propionic anhydride or dicyclohexyl carbodiimide can also be used in this reaction. In case of the use of the latter reactant the dicyclohexyl urea, formed during the reaction, can be separated by filtration from the reaction mixture before work-up.

The second step is preferably carried out by dissolving the crystalline secodicarboxylic anhydride in tetrahydrofuran, cooling to −5° C. and adding a solution of sodium borohydride in dry dimethyl formamide over a period of 2 h, at 0–(−5)° C. The reaction mixture is stirred at 0–(−5)° C. until the completion of the reaction, which is checked by thin layer chromatography, then 10% sulfuric acid solution is added to the mixture over a period of 30 min keeping the temperature below 10° C. Then the reaction mixture is diluted with water and the precipitation of the desired compound is made complete by addition of further sulfuric acid solution. The precipitate is filtered, washed till it is neutral and dried. Instead of sodium borohydride lithium aluminum hydride, lithium tri-tertiary-butoxyaluminohydride or lithium triethylborohydride can be used as complex alkali metal hydride reducing agent.

The process according to our invention can be carried out in the following way, too: the secodicarboxylic acid is dissolved in tetrahydrofuran and after addition of acetic anhydride the reaction mixture is refluxed until the completion of the reaction, then cooled to −5° C. and a solution of sodium borohydride in dry dimethyl formamide is added over a period of 2 h at 0–(−5)° C. The mixture is stirred until the completion of the reaction, which is checked by thin layer chromatography. Then 10% sulfuric acid solution is added over a period of 30 min keeping the temperature below 10° C. After this the reaction mixture is diluted with water and the precipitation of the desired compound is made complete by addition of further sulfuric acid solution. The precipitate is filtered, washed till it is neutral and dried.

Purification of the crude material is carried out by dissolving it in an alkane, alcohol, ketone, ester, nitril or ether type solvent, treating with charcoal, filtering and filtering off the product obtained after concentration of the filtrate. An other possibility is that the crude material is dissolved in a solvent mentioned above, treated with charcoal, filtered, mixed with water and the purified product is obtained with or without evaporation. This way the yield of the oxandrolone is about 80%.

The process according to the invention is illustrated in detail by the following not limiting examples.

EXAMPLE 1

Synthesis of 17β-Hydroxy-17α-methyl-2-oxa-5-androstane-1,3-dione

To a stirred slurn of 10 g (29.5 mmol) of 17β-hydroxy-17α-methyl-1,3-seco-2-nor-5α-androstane-1,3-diacid in 50 ml of tetrahydrofuran 5.6 ml of acetic anhydride was added. After 3 h reflux the completion of the reaction was checked by thin layer chromatography. After completion of the reaction the mixture was concentrated to a volume of 15 ml under reduced pressure, then 50 ml of diisopropyl ether was added. The crystalline suspension was again concentrated to about a volume of 15 ml, then cooled to 5–10° C. and kept at this temperature for 2 h. The crystals were filtered off, washed with dilsopropyl ether at 10° C. and dried at 40° C. in vacuum till the weight was constant to yield 8.9 g (94%) of the title compound. M.p: 184–189° C.

EXAMPLE 2

Synthesis of 17β-Hydroxy-17α-methyl-2-oxa-5α-androstane-1,3-dione

To a stirred solution of 5 g (14.8 mmol) of 17β-hydroxy-17α-methyl-3-seco-2-nor-5α-androstane-1,3-diacid in 30 ml of dry tetrahydrofuran 2.1 ml (16.1 mmol) of propionic anhydride was added. The mixture was refluxed for 1 h, then checked by thin layer chromatography. After completion of the reaction the mixture was concentrated and the residue was recrystallized from diisopropyl ether to yield 4.3 g (90.9%) of the title compound. M.p: 188–190° C.

EXAMPLE 3

Synthesis of 17β-Hydroxy-17α-methyl-2-oxa-5α-androstane-1,3-dione

To a stirred solution of 5 g (14.8 mmol) of 17β-hydroxy-17α-methyl-1,3-seco-2-nor-5α-androstane-1,3-diacid in 25 ml of dry tetrahydrofuran 3.2 g (15.5 mmol) of dicyciohexyl carbodiimide was added. The mixture was stirred at room temperature for 15 min, then checked by thin layer chromatography. After completion of the reaction the precipitated crystals were filtered off, washed with tetrahydrofuran and the filtrate was concentrated. The residue was recrystallized from dusopropyl ether to yield 4.4 g (93%) of the title compound. M.p: 188–190° C.

EXAMPLE 4

Synthesis of 17β-Hydroxy-17α-methyl-2-oxa-5α-androstane-3-one (Reduction With Sodium Borohydride)

A solution of 8.5 (26.5 mmol) of 17β-hydroxy-17α-methyl-2-oxa-5α-androstane-1,3-dione in 170 ml of dimethyl formamide was cooled to 0–5° C. 1.04 g (27.5 mmol) of sodium borohydride was added to the reaction mixture in small portions over a period of 15 min keeping the temperature below 10° C. After the addition the mixture was stirred at 5–10° C. for 15 min, then checked by thin layer chromatography. After completion of the reaction 70 ml (71.4 mmol) of 10% sulfuric acid was added to the reaction mixture over a period of 15 min keeping the temperature below 20° C. After the addition of the sulfuric acid the product started to crystallize. After addition of 1000 ml of water the reaction mixture was stirred for 30 min, the precipitated crystals were filtered off, washed with water and dried at 40° C. till the weight was constant to yield 6.1 g (75.2%) of the crude title compound. M.p: 235–239° C.

EXAMPLE 5

Synthesis of 17β-Hydroxy-17α-methyl-2-oxa-5α-androstane-3-one (Reduction With Lithium Aluminum Hydride)

0.6 g (15.8 mmol) of lithium aluminum hydride was added to 60 ml of dry tetrahydrofuran and the mixture was cooled to −60° C. 5 g (15.6 mmol) of secodicarboxylic acid anhydride in 40 ml of tetrahydrofuran was added dropwise to the mixture over a period of 30 min keeping the temperature at −55±5° C. After the addition the mixture was allowed to warm to 0° C. over a period of 1 h, stirred for 10 min and checked by thin layer chromatography. After completion of the reaction the mixture was cooled to −15° C. and 30 ml of 10% hydrochloric acid was added. Then the mixture was diluted with 300 ml of water and after 30 min stirring the precipitated crystals were filtered off, washed with water and dried at 50° C. till the weight was constant to yield 3.0 g (62.7%) of the crude title compound. M.p: 235–239° C.

EXAMPLE 6

Synthesis of 17β-Hydroxy-17α-methyl-2-oxa-5α-androstane-3-one (Reduction With Lithium Tri-tertiary-butoxyaluminohydride)

8.04 g (31.6 mmol) of lithium tri-tertiary-butoxyaluminohydride was added to 100 ml of dry tetrahydrofuran and the mixture was cooled to −15° C. 5 g (15.6 mmol) of secodicarboxylic acid anhydride in 40 ml of tetrahydrofuran was added dropwise to the mixture over a period of 30 min keeping the temperature at −10±5° C. After the addition the mixture was allowed to warm to 0° C. over a period of 1 h and checked by thin layer chromatography. After completion of the reduction the mixture was cooled to −15° C. and 60 ml of 10% hydrochloric acid was added. Then the mixture was diluted with 450 ml of water and after 30 min stirring the precipitated crystals were filtered off, washed with water and dried at 50° C. till the weight was constant to yield 2.9 g (60.6%) of the crude title compound. M.p: 234-237° C.

EXAMPLE 7

Synthesis of 17β-Hydroxy-17α-methyl-2-oxa-5α-androstane-3-one (Reduction With Lithium Triethylborohydride)

31.6 ml (3.35 g, 31.6 mmol) of 1 M lithium triethylborohydride in tetrahydrofuran was added to 100 ml of dry tetrahydrofuran and the mixture was cooled to −60° C. 5 g (15.6 mmol) of secodicarboxylic acid anhydride in 40 ml of tetrahydrofuran was added dropwise to the mixture over a period of 30 min keeping the temperature at −55±5° C. After the addition the mixture was allowed to warm to 0° C. over a period of 1 H, stirred for 10 min and checked by thin layer chromatography. After completion of the reduction the mixture was cooled to −15° C. and 60 ml of 10% hydrochloric acid was added. Then the mixture was diluted with 450 ml of water and after 30 min stirring the precipitated crystals were filtered off, washed with water and dried at 50° C. till the weight was constant to yield 2.85 g (59.7%) of the crude title compound. M.p: 234–236° C.

EXAMPLE 8

Synthesis of Secodicarboxylic Acid Anhydride and its Reduction Without Isolation With Sodium Borohydride 250 g (0.74 mol) of secodicarboxylic acid was dissolved in 2 l of dry tetrahydrofuran and 90 ml (97.2 g 0.95 mol) of acetic anhydride was added. The mixture was refluxed for 1.5 h and checked by thin layer chromatography. After completion of the reaction the mixture was cooled to −10° C. and 60 g (1.59 mol) of sodium borohydride in 2.0 l of dimethyl formamide was added over a period of 2 h, keeping the temperature at 0–(−10)° C. After the addition the mixture was stirred for 15 min at 0–(−5)° C., then 1 l of 10% sulfuric acid solution was added over a period of 30 min. During the addition of the sulfuric acid the temperature was kept at 10° C. with cooling. Then the reaction mixture was poured into a 20 l reaction vessel, equipped with a stirrer and rinsed with 1 l of water, then a mixture of 61 ml of concentrated sulfuric acid and 12 l of water was added keeping the temperature at 15–20° C. During the addition the crude oxandrolone is precipitating from the mixture. After the addition the pH was checked (pH=1.5±0.5). After 20 min stirring the precipitated crystals were filtered off, washed with 1 l of water and dried at 50° C. till the weight was constant to yield 194.5 g of crude oxandrolone.

The crude oxandrolone was dissolved in a mixture of 4.9 l of ethanol and 16.3 ml of triethy lamine at reflux temperature, treated with 9.7 g of charcoal, the charcoal was flashed with 240 ml of ethanol and the filtrate was concentrated to a volume of 500 ml. The crstalline suspension was cooled to 5° C. and kept at this temperature for 2 h, then filtered and washed with 240 ml of ethanol cooled to 0° C. The wet material was dried at 50° C. till the loss of weight was 0.5% to yield 183.2 g (80.9%) oxandrolone. M.p: 235–239° C.

EXAMPLE 9

Synthesis of Secodicarboxylic Acid Anhydride with Propionic Anhydride and its Reduction Without Isolation With Sodium Borohydride 25 g (0.074 mol) of secodicarboxylic acid was dissolved in 200 ml of dry tetrahydrofuran and 12.24 ml (12.36 g, 0.095 mol) of propionic anhydride was added. The mixture was refluxed for 1.5 h and checked by thin layer chromatography. After completion of the reaction the mixture was cooled to −10° C. and 6 g (0.159 mol) of sodium borohydride in 200 ml of dimethyl formarnide was added over a period of 2 h, keeping the temperature at 0–(−10)° C. After the addition the mixture was stirred for 15 min at 0–(−5)° C. then 100 ml of 10% sulfuric acid solution was added over a period of 30 min. During the addition of the sulfuric acid the temperature was kept at 10° C. with cooling. Then the reaction mixture was poured into a 2 l reaction flask, equipped with a stirrer and rinsed with 100 ml of water. Then a mixtttre of 6.1 ml of concentrated sulfuric acid and 1.2 l of water was added (keeping the temperature at 15–20° C.). During the addition the crude oxandrolone is precipitating from the mixture. After the addition the pH was checked (pH=1.5±0.5). After 20 min stirring the precipitated crystals were filtered off, washed with 200 ml of water and dried at 50° C. till the weight was constant to yield 19.4 g of crude oxandrolone.

The crude oxandrolone was dissolved in a mixture of 490 ml of ethanol and 1.63 ml of triethylamine at reflux temperature treated with 1.0 g of charcoal, the charcoal was washed with 24 ml of ethanol and the filtrate was concentrated to a volume of 50 ml. The crystalline suspension was cooled to 5° C. and kept at this temperature for 2 h, then filtered and washed with 24 ml of ethanol cooled to 0° C. The wet material was dried at 50° C till the loss of weight was 0.5% to yield 18.3 g (80.8%) of oxandrolone. M.p: 235–239° C.

EXAMPLE 10

Recrystallization of Oxandrolone From Isopropanol 5.0 of crude oxandrolone was recrystallized from isopropanol, which contains 0.5% of triethylamine by dissolving at reflux temperature to yield 4.7 g (94%) of pure oxandrolone. M.p: 240–242° C.

EXAMPLE 11

Recrystallization of Oxandrolone From a Mixture of Ethanol and Water 5.0 g of crude oxandrolone was dissolved in 100 ml of ethanol at reflux temperature and 100 ml of water was added, which contained 1% of triethylamine. The mixture was cooled to 0° C. and the precipitated product was filtered off to yield 4.8 g (96%) of pure oxandrolone. M.p: 237–239° C.

What is claimed is:

1. Process for the synthesis of 17β-hydroxy-17α-methyl-2-oxa-5α-androstane-3-one of the formula (I)

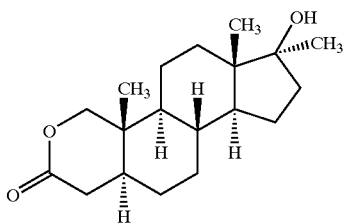

(I)

characterised by transforming the 17β-hydroxy-17α-methyl-1,3-seco-2-nor-5α-androstane-1,3-diacid of formula (III)

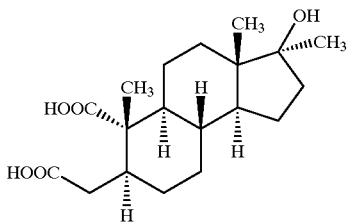

(III)

into the ring-closed 17β-hydroxy-17α-methyl-1,3-seco-2-nor-5α-androstane-1,3-diacid anhydride of formula (II)

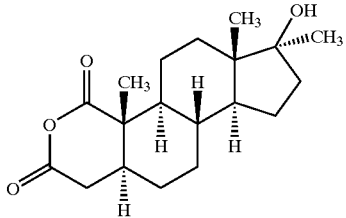

(II)

in an inert solvent or without solvent with a $C_2$–$C_3$ alkane acid anhydride or a substituted carbodiimide of formula $R^1$—N=C=N—$R^2$— wherein $R^1$ and $R^2$ independently are $C_1$–$C_6$ alkyl group, $C_1$–$C_6$ alkyl group substituted by tertiary or quaternary amino group or 1–3 phenyl group, $C_5$–$C_6$ cycloalkyl group, aryl group substituted by 1–3 methoxy, tertiary-amino, nitro, $C_1$–$C_4$ alkyl group or 1–3 halogen atom—and regioselectively reducing it by a complex alkali metal hydride in an inert solvent.

2. The process in claim 1, characterised by carrying out the cyclisation with acetic anhydride.

3. The process in claim 1, characterised by carrying out the cyclisation with propionic anhydride.

4. The process in claim 1, characterised by carrying out the cyclisation with dicyclohexyl carbodiimide.

5. The process in claim 1, characterised by carrying out the cyclisation in dry tetrahydrofuran.

6. The process in claim 1, characterised by carrying out the reduction with sodium borohydride.

7. The process in claim 1, characterised by carrying out the reduction with lithium aluminum hydride.

8. The process in claim 1, characterised by carrying out the reduction with lithium tri-tertiary butoxyaluminohydride.

9. The process in claim 1, characterised by carrying out the reduction with lithium triethylborohydride.

10. The process in claim 6, characterised by carrying out the reduction in dry tetrahydrofuran or dimethyl formamide.

11. The process in claim 1, characterised by carrying out the reduction of 17β-hydroxy-17α-methyl-1,3-seco-2-nor-5α-androstane-1,3-diacid anhydride of formula (II), which is formed in the cyclisation, without isolation.

12. 17β-Hydroxy-17α-methyl-1,3-seco-2-nor-5α-androstane-1,3-diacid anhydride of formula (II).

* * * * *